United States Patent [19]
Joffe et al.

[11] Patent Number: 5,856,198
[45] Date of Patent: Jan. 5, 1999

[54] PERFORMANCE MONITORING OF GAS-PHASE AIR FILTERS

[75] Inventors: Michael A. Joffe, Millis, Mass.; Devon A. Kinkead, Cumberland, R.I.

[73] Assignee: Extraction Systems, Inc., Woonstocket, R.I.

[21] Appl. No.: 639,715

[22] Filed: Apr. 29, 1996

Related U.S. Application Data

[63] Continuation of Ser. No. 365,213, Dec. 28, 1994, abandoned.

[51] Int. Cl.$^6$ ..................................................... G01N 29/02
[52] U.S. Cl. .................... 436/100; 422/82.01; 422/88; 73/31.03
[58] Field of Search ................... 73/24.06, 313, 73/23.2, 31.03; 422/82.01, 83, 88; 436/100

[56] References Cited

U.S. PATENT DOCUMENTS

| | | |
|---|---|---|
| 3,753,656 | 8/1973 | Matson et al. . |
| 3,870,495 | 3/1975 | Dixson et al. . |
| 3,911,413 | 10/1975 | Wallace ............................ 340/237 R |
| 4,437,391 | 3/1984 | Eguchi et al. . |
| 4,530,272 | 7/1985 | Stokes . |
| 4,558,636 | 12/1985 | Malmstrom et al. . |
| 4,595,575 | 6/1986 | Oeste et al. . |
| 4,642,296 | 2/1987 | Hubner . |
| 4,693,173 | 9/1987 | Saiki et al. . |
| 4,737,173 | 4/1988 | Kudirka et al. . |
| 4,847,594 | 7/1989 | Stetter ...................................... 340/540 |
| 4,873,914 | 10/1989 | Hirayama . |
| 4,873,970 | 10/1989 | Freidank et al. ................... 128/202.22 |
| 4,895,017 | 1/1990 | Pyke et al. ..................................... 73/23 |
| 5,030,423 | 7/1991 | Obee et al. . |
| 5,042,997 | 8/1991 | Rhodes . |
| 5,053,064 | 10/1991 | Hama et al. . |
| 5,074,137 | 12/1991 | Harris et al. . |
| 5,096,477 | 3/1992 | Shinoda et al. . |
| 5,181,819 | 1/1993 | Sakata et al. . |
| 5,208,162 | 5/1993 | Osborne et al. ................................ 436/6 |
| 5,213,767 | 5/1993 | Smith et al. . |
| 5,320,577 | 6/1994 | Tooru et al. . |
| 5,325,705 | 7/1994 | Tom ............................................ 73/31.03 |

FOREIGN PATENT DOCUMENTS

| | | |
|---|---|---|
| 27 43 107 A1 | 9/1977 | Germany . |
| 55-134240 A | 10/1980 | Japan . |
| 62-73023 | 4/1987 | Japan . |
| 89-152266 | 6/1989 | Japan . |
| 2-203139 | 8/1990 | Japan . |
| 2 005 016 | 11/1979 | United Kingdom . |
| WO 90/05549 | 5/1990 | WIPO . |

OTHER PUBLICATIONS

Weschler et al., Ozone–Removal Efficiencies of Activated Carbon Filters After More Than Three Years of Continuous Service, ASHRAE Transactions, Vo. 100, Pt. 2, Jun. 25, 1994.

(List continued on next page.)

*Primary Examiner*—Lyle A. Alexander
*Attorney, Agent, or Firm*—Fish & Richardson P.C.

[57] ABSTRACT

A scheme for monitoring the performance of a gas-phase filter in which upstream and downstream detection surfaces are exposed to upstream and downstream air so that molecular contamination may respectively form non-volatile residue thereon, and the performance of the air filter is determined based on the ratio of the amount of non-volatile residue respectively forming on the upstream and downstream detection surfaces. In another embodiment, a first electrical signal is provided representative of the amount of non-volatile residue forming on the upstream detection surface, a second electrical signal is provided representative of the amount of non-volatile residue forming on the downstream detection surface, and the performance of the air filter is determined in real-time based on the first and second electrical signals that are provided. The detection surfaces of the upstream and downstream detectors may be selected so that the mass of non-volatile residue forming thereon may be determined, either in real-time or by subsequent chemical analysis.

33 Claims, 10 Drawing Sheets

OTHER PUBLICATIONS

A. Lieberman, "Gas Filter Testing Methods", Contamination Control & Clean Rooms, 1992.

Turk et al., "Tracer Gas Nondestructive Testing of Activated Carbon Cells", Materials Research & Standards, Nov. 1969.

"The Passive Bubbler", A User's Manual, Version 2.1, SKC, Apr. 1992.

"Piezoelectric Gas Phase Detection" Universal Sensors, Inc., Apr. 1992.

"3M Organic Vapor Monitors #3520/3530 with Back–up Section Instructions for Use", 3M Occupational Health and Environmental Safety Division, Oct. 1991.

"Determination of Selected Organic Vapors in Air", 3M Company, Occupational Health & Environmental Safety Division, Dec. 1991.

Bowers et al., "A 200 MHz surface acoustic wave resonator mass microbalance", Rev. Sci. Instrum., 62(6), Jun. 1991.

Shields et al., "Analysis of Ambient Concentrations of Organic Vapors with a Passive Sampler", APCA Journal, vol. 37, No. 9, Sep. 1987.

Yanagisawa et al., "A Badge–Type Personal Sampler for Measurement of Personal Exposure to $NO_2$ and NO in Ambient Air", Environmental International, vol. 8, pp. 235–242, 1982.

Wohltjen et al., Surface Acoustic Wave Probe for Chemical Analysis. I. Introduction and Instrument Description, Analytical Chemistry, vol. 51, No. 9, pp. 1458–1464, Aug. 1979.

Wohltjen et al., Surface Acoustic Wave Probes for Chemical Analysis. II. Gas Chromatography Detector Analytical Chemistry, vol. 51, No. 9, pp. 1465–1470, Aug. 1979.

Wohltjen et al., Surface Acoustic Wave Probes for Chemical Analysis. III. Thermomechanical Polymer Analyzer, Analytical Chemistry, vol. 51, No. 9, pp. 1470–1475, Aug. 1979.

Advertisement, "The Badge of the 90's" (Before Dec. 1993).

OnGuard, Electronic Corrosion Sensor, Purafil (Before Dec. 1993).

Advertisement, "Assessment of Environmental Corrosivity", Extraction Systems, Inc. (1992).

Advertisement, "Copper or Silver–Reactivity Coupons Exposure Procedure", Extraction Systems, Inc. (1992).

Advertisement, "Filtercheck", Extraction Systems, Inc. (1992).

David Jenson, "Statement of the Contamination Control Industry", Microcontamination Conference 1992.

Mori et al., "Correlating Organophosphorus Contamination on Wafer Surfaces with Hepa–Filter Installation", Microcontamination Nov. 1992.

MacDonald et al., "Airborne Chemical Contamination of a Chemically Amplified Resist", SPIE vol. 1466 Advances in Resist Technology and Processing VIII (1991).

Muller et al., "Measurement of Airborne Concentrations and Surface Arrival Rates of Organic Contaminants in Clean Rooms", AT&T Bells Labs, Murray Hill, NJ 07974 1993.

Muller et al., "Detection and Sources of Volatile Clean Room Contaminants", AT&T Microelectronics, 555 Union Boulevard, Allentown, PA 18103 (1993).

Brochure, Aire–Lab: Corrosion Monitoring Results, Extraction Systems, Inc. (1992).

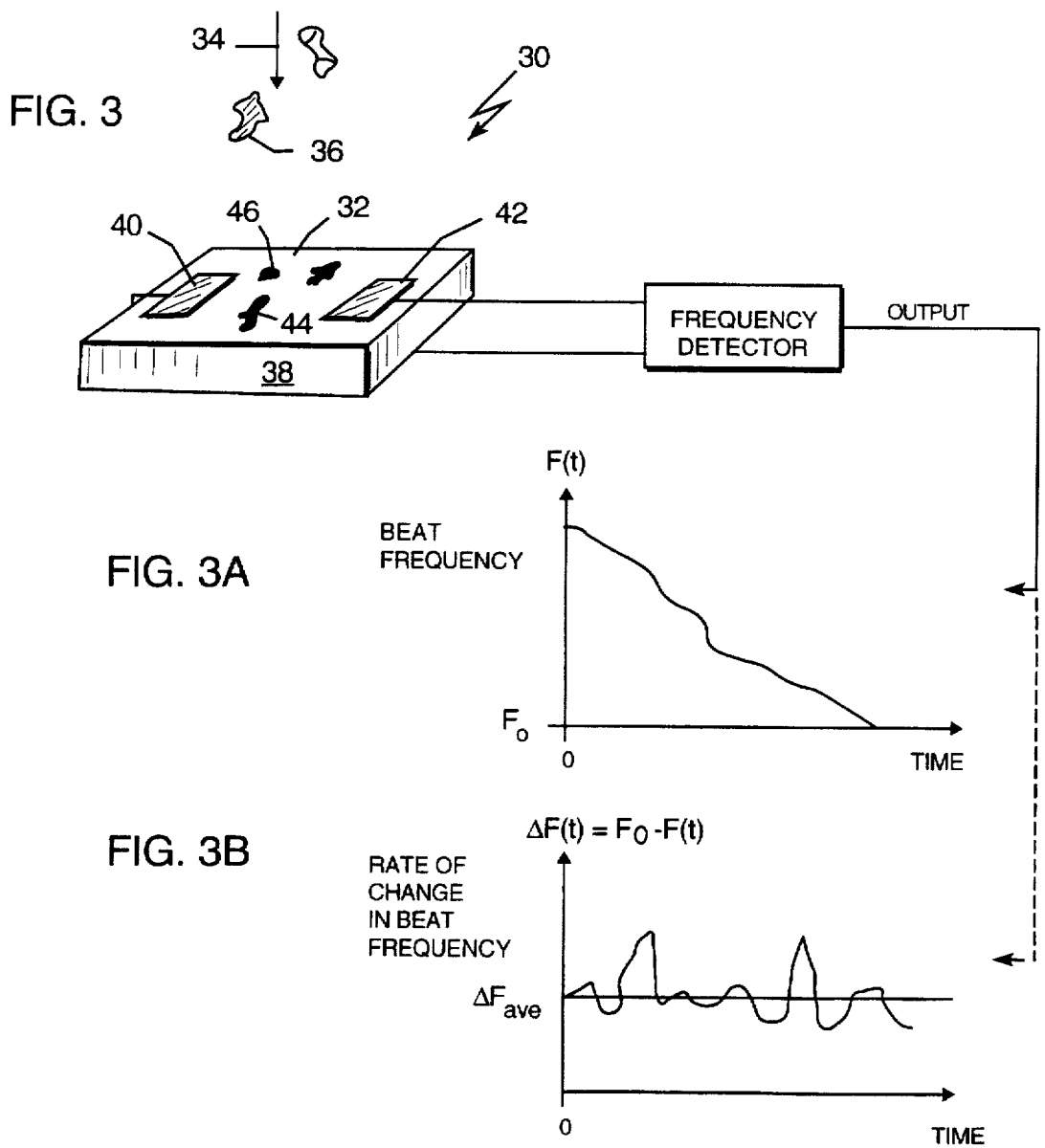

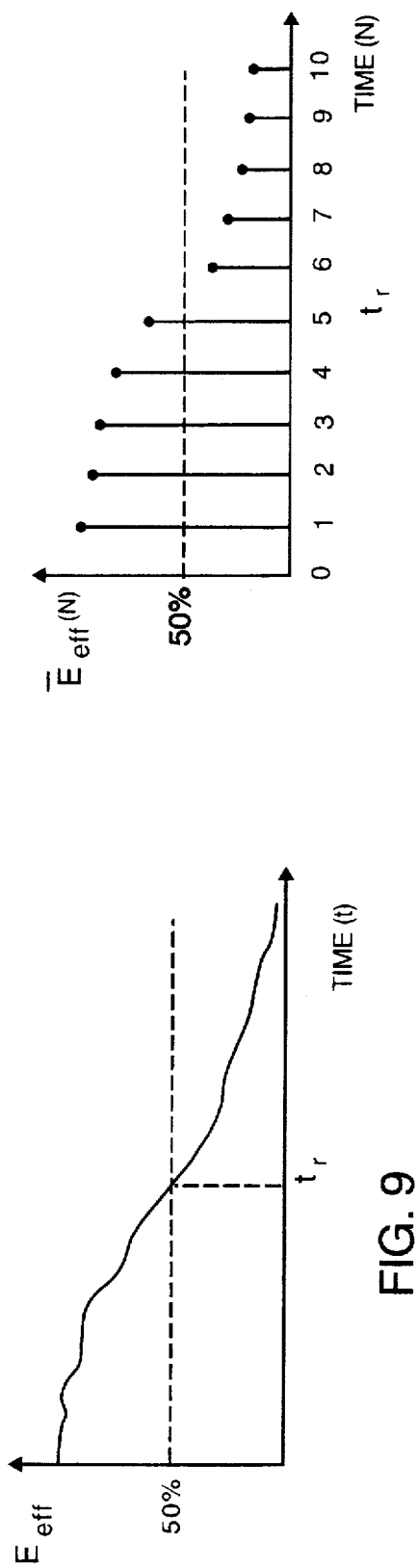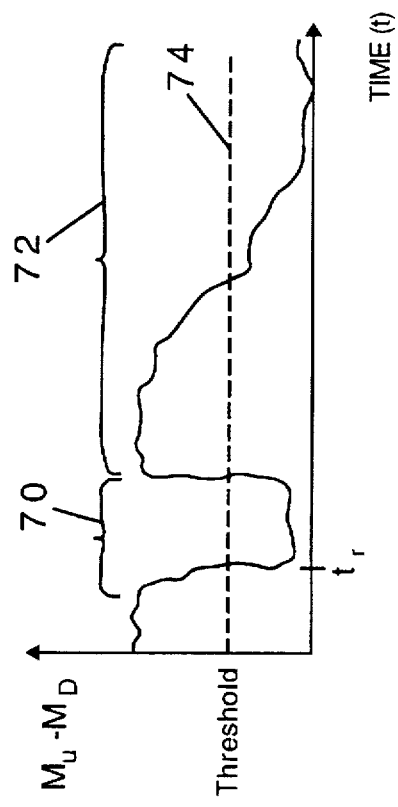

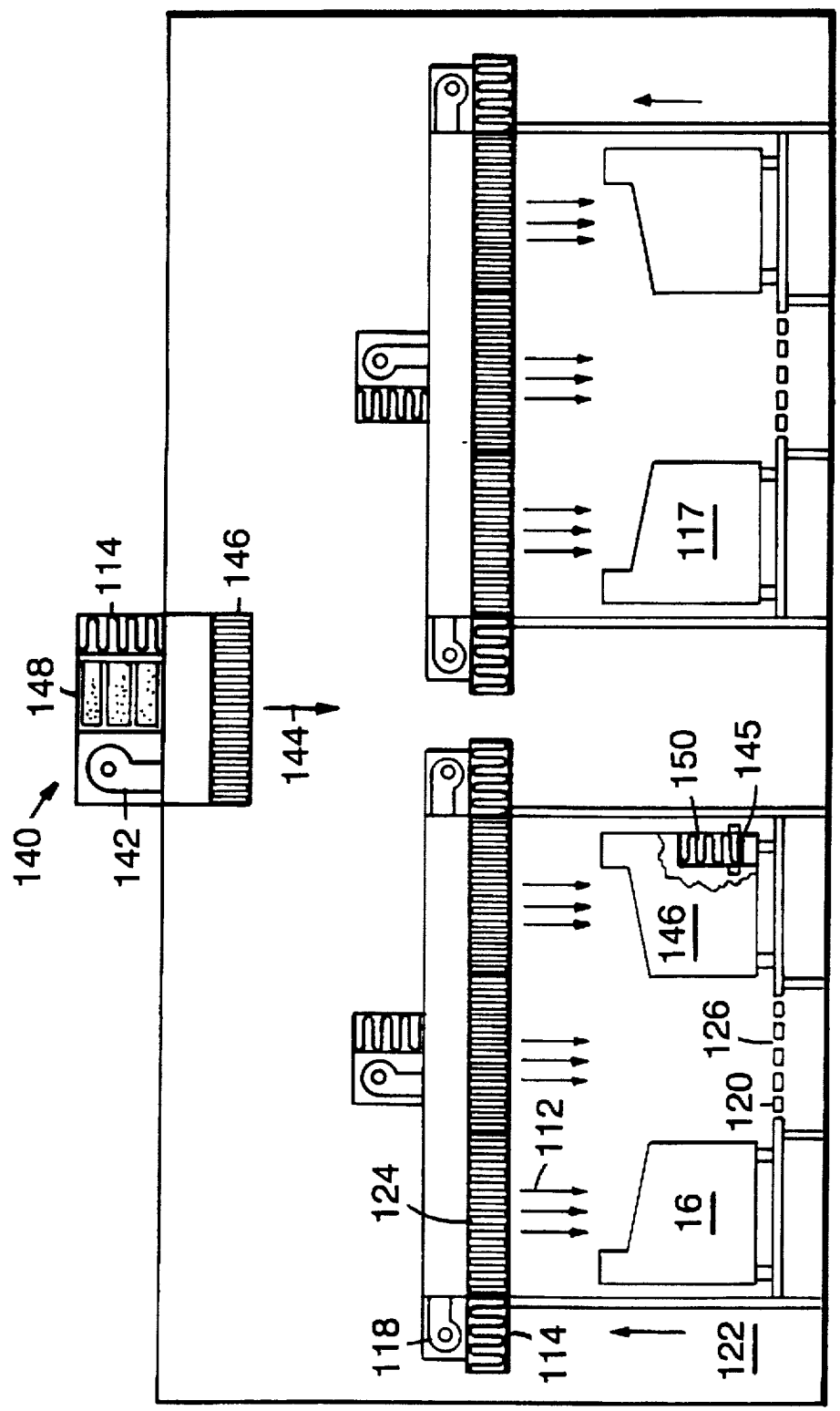

1

PERFORMANCE MONITORING OF GAS-PHASE AIR FILTERS

This is a continuation of application Ser. No. 08/365,213, filed Dec. 28, 1994, now abandoned.

BACKGROUND

This invention relates to performance monitoring of gas-phase air filters.

Performance monitoring of gas-phase air filters is particularly important in many environments, including semiconductor fabrication clean environments, museums, archives, petrochemical plants, refineries, wastewater treatment facilities, airport terminals, office buildings in urban areas, and hospitals. For example, the presence of even low levels of corrosive gases and vapors threatens cultural property and capital equipment including computer control systems, manufacturing tools, electrical systems, and facility mechanical equipment. The performance of gas-phase air filters used in these environments must be monitored to determine when the filters are not filtering at acceptable levels and should be replaced.

Air filtering is critical within an environment that must remain clean, such as a semiconductor device manufacturing environment (cleanroom), which is sensitive to low levels of gas-phase (molecular) contamination. Examples of process-limiting molecular contaminants include: acids, such as hydrochloric acid, nitric acid, phosphoric acid, hydrobromic acid; bases, such as ammonia, ammonium hydroxide, tetramethylammonium hydroxide, trimethylamine, triethylamine, hexamethyldisilazane, NMP, cyclohexylamine, diethylaminoethanol, methylamine, dimethylamine, ethanolamine, morpholine, condensables, such as silicones and hydrocarbons with a boiling point greater than or equal to 150° C.; and dopants, such as boron (usually as boric acid), phosphorus (usually as organophosphate), and arsenic (usually as arsenates).

Performance monitoring of gas-phase air filters is also particularly important in areas where even low concentration levels of toxic gases and irritants threaten health and safety of people. Proper monitoring is important to ensure timely filter replacement to maintain necessary air cleanliness.

SUMMARY

In one aspect, the invention features a scheme for monitoring the performance of a gas-phase filter positioned in an air stream, which may be subject to molecular contamination, and useful for removing molecular contamination therefrom, in which: an upstream detection surface is exposed to the airstream at a location upstream of the air filter so that upstream molecular contamination may form a non-volatile residue on the exposed upstream detection surface over time; a downstream detection surface is exposed to the airstream at a location downstream of the air filter so that downstream molecular contamination may form a non-volatile residue on the exposed downstream detection surface over time; the amount of non-volatile residue respectively forming on the exposed upstream and downstream detection surfaces is determined; and the performance of the air filter is determined based on the ratio of the amount of non-volatile residue respectively forming on the exposed upstream and downstream detection surfaces.

In another aspect, a first electrical signal is provided representative of the amount of non-volatile residue forming on the upstream detection surface, a second electrical signal is provided representative of the amount of non-volatile residue forming on the downstream detection surface, and the performance of the air filter is determined in real-time based on the first and second electrical signals that are provided.

In yet another aspect, the invention features a filter monitor comprising: an upstream detector having a detection surface exposed to the airstream at a location upstream of the air filter so that molecular contamination may form a non-volatile residue on the exposed detection surface of the upstream detector, the upstream detector having an output for providing a signal representative of the amount of non-volatile residue forming on the detection surface of the upstream detector; a downstream detector having a detection surface exposed to the airstream at a location downstream of the air filter so that molecular contamination may form a non-volatile residue on the exposed detection surface of the downstream detector, the downstream detector having an output for providing a signal representative of the amount of non-volatile residue forming on the downstream detector; and a comparator having an input coupled to the upstream and downstream detectors and having an output for providing an output signal representative of the performance of the air filter based on the ratio of signals received from the upstream and downstream detectors.

In a further aspect, the invention features a filter monitor comprising: an upstream detector having a detection surface exposed to the airstream at a location upstream of the air filter so that molecular contamination may form a non-volatile residue on the exposed detection surface of the upstream detector, the detection surface of the upstream detector being selected so that the mass of non-volatile residue forming on the detection surface of the upstream detector may be determined; and a downstream detector having a detection surface exposed to the airstream at a location downstream of the air filter so that molecular contamination may form a non-volatile residue on the exposed detection surface of the downstream detector, the detection surface of the downstream detector being selected so that the mass of non-volatile residue forming on the detection surface of the downstream detector may be determined.

Embodiments of the invention may include one or more of the following features. Determining the performance of the air filter may comprise determining an effective efficiency ($\epsilon_{\mathit{eff}}$) of the filter as defined by $$\epsilon_{\mathit{eff}} = \frac{M_{upstream} - M_{downstream}}{M_{upstream}}$$

wherein $M_{upstream}$ and $M_{downstream}$ are the amount of non-volatile residue formed on the upstream and downstream detection surfaces respectively. Alternatively, determining the performance of the air filter may comprise determining the rates of change in the amounts of non-volatile residues forming on the upstream and downstream detection surfaces over preselected sequential intervals of time. Determining the rates of change preferably further comprises determining an effective efficiency ($\epsilon_{\mathit{eff}}$) of the filter as defined by $$\epsilon'_{\mathit{eff}} = \frac{\Delta m_{upstream} - \Delta m_{downstream}}{\Delta m_{upstream}}$$

wherein $\Delta m_{upstream}$ and $\Delta m_{downstream}$ are the changes in the amounts of non-volatile residues formed on the upstream and downstream detection surfaces during a preselected interval of time. Determining the amount of non-volatile residue may comprise determining the mass of non-volatile residue respectively forming on the exposed upstream and downstream detection surfaces. Determining the amount of non-volatile residue may comprise generating electrical signals representative of the amount of non-volatile forming on the detection surfaces.

In certain preferred embodiments, exposing upstream and downstream detection surfaces to the airstream comprises the step of providing a mass microbalance sensor. Preferably, the step of providing a mass microbalance sensor comprises providing a surface acoustic wave mass microbalance. The mass microbalance sensor may be a piezoelectric crystal mass microbalance that is constructed and arranged as a resonator or as a delay line.

In certain other preferred embodiments, the upstream detection surface and the downstream detection surface respectively comprise adsorbent material separated from the airstream by a diffusion barrier constructed and arranged to establish a diffusion gradient between the adsorbent material and the airstream. Preferably, the gas-phase filter comprises adsorbent media and the adsorbent media of the upstream detection surface and the downstream detection surface comprises substantially the same kind of adsorbent media.

The upstream and downstream detection surfaces are preferably sensitive to levels of molecular contamination in the concentration range of 1 ppm to 1 ppb, or less. The upstream and downstream detection surfaces may be sensitive to organic condensables. The upstream and downstream detection surfaces may be selected so that a preselected type of molecular contamination preferentially forms a non-volatile residue on the exposed upstream and downstream detection surfaces. For example, the upstream and downstream detection surfaces may be treated with a reagent comprising a base so that acid vapors preferentially form non-volatile residues thereon. The upstream and downstream detection surfaces may instead be treated with a reagent comprising an acid so that basic vapors preferentially form non-volatile residues thereon.

Systems of filters and associated filter monitors that are adapted for particular environments and applications are also contemplated.

Among the advantages of the invention are the following. The invention provides a filter monitoring scheme that can provide a real-time determination of filter performance and provides a quantitative measure of filter performance. This is especially useful for filtering in environments that are sensitive to low levels of molecular contamination and must use filters with efficiencies above selected threshold values. Furthermore, since the filter monitors provide electrical signals that can be send to a central processor, the performance of a large number of filters can be easily monitored in real-time. The present invention provides a scheme for monitoring the performance of gas-phase filters installed in environments susceptible to degradation by low-concentrations of gas-phase contaminants. In such environments it is important to accurately monitor the performance of the filtration system to prevent exposure to process-limiting or otherwise harmful gas-phase contamination.

Other features and advantages will become apparent from the following description and from the claims.

DESCRIPTION

FIG. 3 is a diagrammatic perspective view of a detector. FIGS. 3A and 3B are plots of beat frequency and rate of change in beat frequency over time, respectively.

FIGS. 9 and 9A are plots of continuous and sampled filter effective efficiencies over time, respectively.

FIG. 10 is a plot of the difference in magnitude of the rate of non-volatile residue formation upstream and the amount of non-volatile residue formed downstream over time.

FIGS. 12 and 12A are a diagrammatic perspective view and a diagrammatic side view of a cleanroom.

Figure 1:
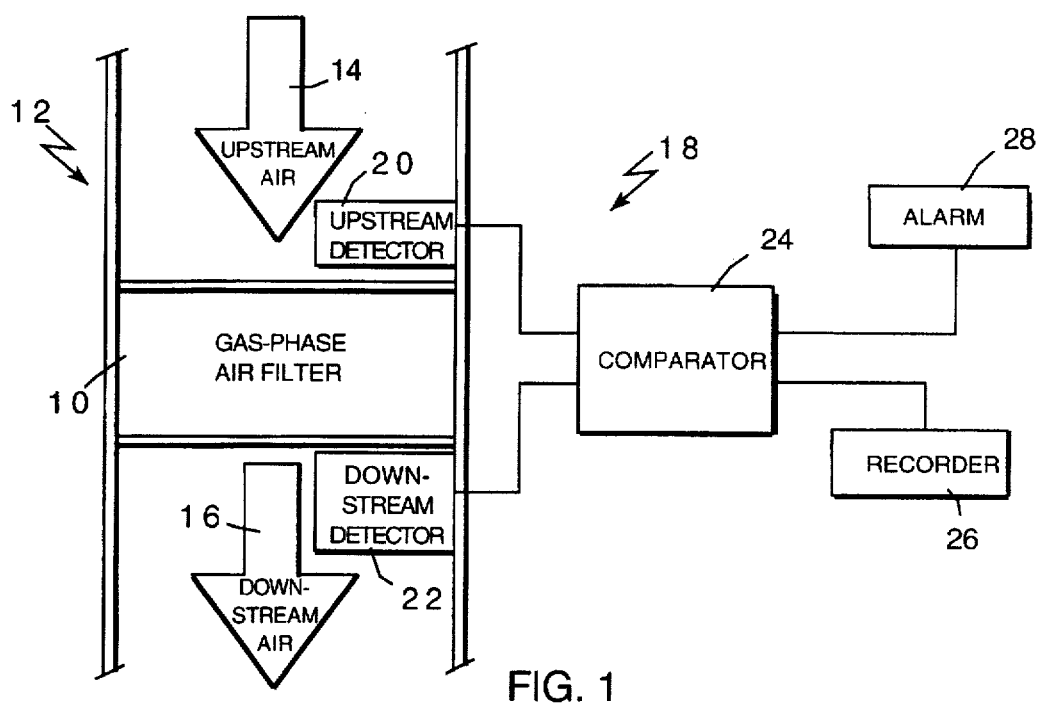
FIG. 1 is a diagrammatic side view of an air handling system including a gas-phase filter and a filter monitor.

Referring to FIG. 1, a gas-phase air filter 10 in an air handling system 12 is positioned to receive an incoming airstream 14 that may be subject to molecular contamination. Air filter 10 includes adsorbent media that is selected to substantially remove the molecular contamination in one or more passes to provide to a downstream location an outgoing airstream 16 that is substantially free of the molecular contamination. A filter monitor 18 including upstream and downstream detectors 20, 22 is used to monitor the performance of the gas-phase filter, e.g., to determine when air filter 10 has reached the end of its useful service life and should be replaced.

Detectors 20 and 22 have respective detection surfaces which are selected to detect the molecular contamination in the incoming and outgoing air streams. In particular, the detection surfaces are selected so that molecular contamination in the vicinity of the detection surfaces may form non-volatile residues on the surfaces, which can be subsequently detected. The rate at which non-volatile residue forms on a detection surface is representative of the concentration of molecular contamination in the airstream in the vicinity of the detection surface.

As used herein we intend the term "non-volatile residue" to broadly refer to a solid that forms onto a surface from the gas-phase and does not readily pass off by evaporation. Formation of a non-volatile residue may be the result of condensation or the result of a chemical reaction at the surface.

Upstream detector 20 is positioned in the air stream at a location upstream of the air filter and downstream detector 22 is positioned in the air stream at a location downstream of the air filter. The precise locations of the upstream and downstream detectors can be varied. However, it is important for the detection surfaces of the detectors to be exposed to the air streams. Generally, there is sufficient turbulence in the air streams to disrupt boundary layers at the detection surfaces. However, one or more baffles may be installed to increase the turbulence in the air streams.

Upstream and downstream detectors 20, 22 may produce signals indicative of the amounts of non-volatile residue that has formed on the detection surfaces, depending on the kind of detector selected. These signals are received by a comparator 24 (e.g., a computer) which calculates the ratio of the received signals to determine the effective efficiency (defined below) of gas-phase filter 10. The calculated effective efficiency is stored in a recorder 26 (e.g., a computer database or a chart recorder) over time. If the value of the effective efficiency is less than a predetermined threshold value, the comparator sends a signal to an alarm 28 indicating that the filter should be replaced.

Figure 2:
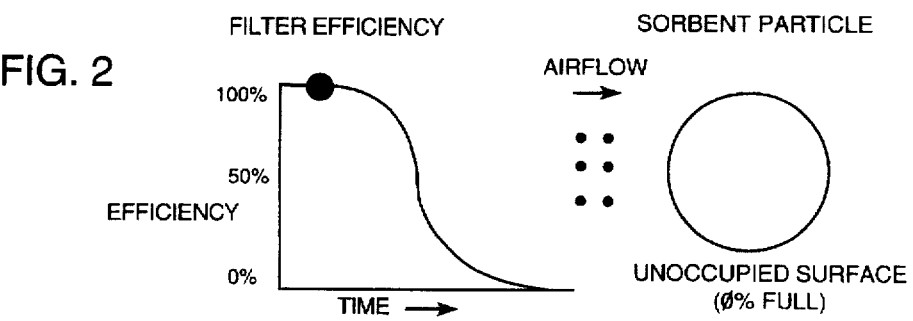
FIGS. 2, 2A and 2B are plots of filter efficiency over time and associated diagrammatic views of sorbent particles at three different times.
Figure 2A:
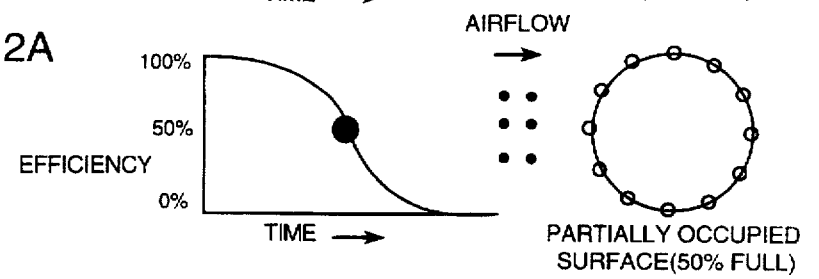
Figure 2B:
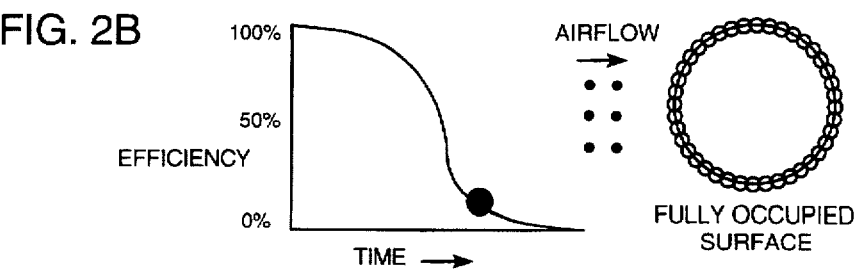

Referring to FIGS. 2–2B, over the service life of an adsorbent-based gas-phase air filter that is exposed to low levels of molecular contamination (e.g., in the ppb to ppm range), the filtering efficiency of the filter gradually decreases as molecular contamination adsorbs onto the surfaces of the constituent sorbent particles (as shown diagrammatically in the drawings located to the right of each of the plots of filter efficiency). Adsorbent-based filters operate on the principles of diffusion and the diffusion gradient. Diffusion delivers molecular contamination to the surfaces of the adsorbent particles and provides the mechanism by which the contamination penetrates the exterior surfaces of the particles. At low concentration levels (less than 10 ppm), the diffusion gradient is low and diffusion into the adsorbent particles occurs at a rate much lower than the rate at which molecular contamination forms onto the surfaces of the adsorbent particles. This causes a drop in filter efficiency over time, as the surface area of the adsorbent particles available for adsorption is used up by adhering adsorbate (non-volatile residue formed on the surface of a sorbent).

Ideally, the filtering efficiency ($\epsilon$) of a gas-phase air filter can be defined by $$\epsilon(t) \equiv \frac{C_{upstream}(t) - C_{downstream}(t)}{C_{upstream}(t)} \quad (0 \leq \epsilon \leq 1) \quad (1)$$

where $C_{upstream}(t)$ and $C_{downstream}(t)$ are the molecular contamination concentrations in the airstream upstream and downstream of the air filter, respectively. Unless otherwise indicated, the term "efficiency" refers to first pass efficiency.

However, we have realized that whether a particular class or species of molecular contamination will form a non-volatile residue on a particular detection surface depends on a number of factors in addition to the molecular contamination concentration, including the reactivity of the detection surface with respect to the molecular contamination and the amount of non-volatile residue previously formed on the detection surface. We have also realized that environmental conditions such as temperature, humidity, and pressure will affect the detectivity of the surface.

Monitors

In monitoring the performance of a filter it is not generally known what contamination the filter will be exposed to during use. In general, the filter monitor is selected based on the filter to be monitored and for effective monitoring it is important to: (a) determine the contaminants or groups of contaminants that are present; (b) of those present, determine the contaminant or contaminants that are representative of the performance of the filter to be monitored (i.e., determine which contaminants are being filtered by the filter); and (c) determine an appropriate passive monitor for the representative contaminant. As used herein, the term "passive monitor" refers generally to a monitor that can be deployed in the field for a substantially long time (e.g., up to at least a few months) and required little maintenance prior to replacement.

Mass Microbalance Monitor

Referring to FIG. 3, a detector 30, which may be used as upstream detector 20 or downstream detector 22, includes a detection surface 32, which is exposed to an incoming air stream 34 including molecular contamination 36. In a presently preferred embodiment, detection surface 32 is formed from a piezoelectric crystal 38 and is configured as a mass microbalance resonator sensor, as described in W. D. Bowers et al., "A 200 MHz surface acoustic wave resonator mass microbalance," Rev. Sci. Instrum., Vol. 62, June 1991, which is herein incorporated by reference. The frequency of vibration is related to the way the crystal is cut and to the amount of mass formed on (and surface area of) detection surface 32. Leads 40, 42 are used to apply time-varying electrical signals to piezoelectric crystal 38. Leads 40, 42 are also used to detect a shift in the resonant frequency of the detector. Alternatively, detector 30 may be configured as a delay line, as described in H. Wohltjen et al., "Surface Acoustic Wave Probe for Chemical Analysis," Analytical Chemistry, Vol. 51, No. 9, pp. 1458–1475 (August 1979).

Even when detection surface 32 is exposed to an air stream having a constant concentration of molecular contamination, the measured rate of change of formed non-volatile residue will vary depending on environmental conditions, e.g., temperature and humidity. The amount of deposited (formed) material will also depend on other parameters, e.g., the amount of material previously deposited onto the surface. We believe the detectivity D(t) of a detection surface depends on $$D(t) = K_1 \cdot S(T, RH, R, A(t)) \quad (2)$$

where, $K_1$ is a constant, S(T, RH, R, A(t)) is a "sticking coefficient" that depends on (among other things) the temperature (T), the relative humidity (RH), the reactivity (R) of the surface with the molecular contamination, and A(t) which is the effective surface area of the detection surface which decreases over time (t). The sticking coefficient (S) represents a probability that molecular contamination in the vicinity of the detection surface will condense from the gas-phase and adhere onto the detection surface.

Molecular contamination 36 may simply condense from the gas-phase onto the surface of detector 30 to form a non-volatile residue 44 (FIG. 3). Also, selective adsorption of a particular class of molecular contamination may be achieved, e.g., by applying to the detection surface a thin film (coating) of a selectively adsorbing material. Thus, when exposed to molecular contamination, some of the molecular contamination may be adsorbed on the detection surface of the detector as a non-volatile reaction product residue 46. The deposited non-volatile residue 44 and non-volatile reaction product residue 46 increase the mass on the detection surface that is measured as a resonant frequency shift.

The decrease in frequency following an increase in mass ($\Delta m$) of an oscillating crystal, is given by:

$$\Delta f = -\frac{2.3 \times 10^{-6}}{A} \cdot F_0^2 \cdot \Delta m \quad (3)$$

where $\Delta f$ is the change in frequency, $F_0$ is the fundamental frequency applied to the crystal, $\Delta m$ is the change in mass of the detection surface caused by formed non-volatile residue, and A is the area of the detection surface (typically on the order of 1 cm$^2$). This can be summarized by $$\Delta f = -K \cdot \Delta m \quad (4)$$

where K is a constant ($K = 2.3 \times 10^{-6} F_0^2 / A$). The resonant frequency as a function of time (f(t)) can be expressed as $$f(t) = F_0 - K \cdot M(t) \quad (5)$$

Accordingly, the variation in the mass over time (M(t)) can be expressed in terms of the resonant frequency $$M(t) = \frac{f_0 - f(t)}{K} \quad (6)$$

Therefore, under ideal conditions changes in frequency are proportional to the change in mass of the detection surface. Such piezoelectric sensors are useful, at least in part, because of their small size and low detection limits (the lowest detection level is generally in the ppb region, with linearity to ppm). Low-level detection sensitivity is especially important in an environment in which low levels of molecular contamination are severely detrimental (e.g., in a semiconductor device fabrication area or a work environment that may be subject to gas-phase contaminants that are corrosive or toxic at low concentration levels). Such detectors should typically be replaced after a period of about six months to one year, depending on the molecular contamination concentration exposure level.

Referring to FIGS. 3A and 3B, the measured beat frequency of detector 30 changes over time as non-volatile residues form on surface 32. The rate of change in the beat frequency provides a measure of the rate of change in the formed mass over time ($\Delta$m).

An effective efficiency ($\epsilon_{\mathit{eff}}(t)$) may be determined by measuring the resonant frequency (f(t); FIG. 3A)) to determine the amount of non-volatile residue that has formed on a detection surface and by using equation (7), below.

$$\epsilon_{\mathit{eff}}(t) = \frac{M_{upstream}(t) - M_{downstream}(t)}{M_{upstream}(t)} \quad (7)$$

An alternative measure of effective efficiency ($\epsilon'_{\mathit{eff}}(t)$) may be determined from the measured rate of change of the resonant frequency ($\Delta f$; FIG. 3B) and by using equation (8), below.

$$\epsilon'_{\mathit{eff}}(t) \equiv \frac{\Delta m_{upstream} - \Delta m_{downstream}}{\Delta m_{upstream}} \quad (8)$$

Other Monitors

In all of the following detectors a membrane is used to control exposure of the collecting media to the molecular contamination and makes possible quantitative measurements. The collecting media (e.g., activated carbon, reagent solution, or water) varies, depending on the kind of molecular contamination that is to be monitored.

Organic Vapor Monitor

For monitoring volatile organic contaminants, such as toluene, benzene, and vapors of other low boiling point solvents, a detector 30 (e.g., an Organic Vapor Monitor available from 3M Company of St. Paul, Minn., under the Brand Nos. 3500, 3510, 3520, and 3530, and described in H.C. Shields et al., "Analysis of ambient concentrations of organic vapors with a passive sampler," APCA Journal, Vol. 37, No. 9, (September 1987), wherein is herein incorporated by reference), may be used as upstream detector 20 or downstream detector 22.

Figure 4:
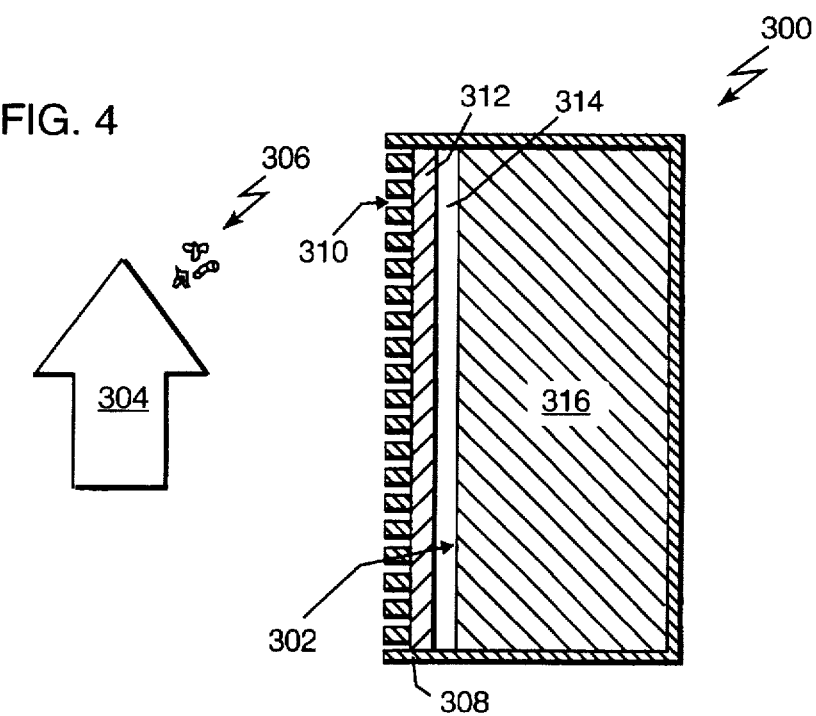
FIG. 4 is a diagrammatic cross-sectional side view of a detector.

Referring to FIG. 4, detector 300 includes a detection surface 302, which is exposed to an incoming air stream 304 including molecular contamination 306 through a housing 308 with a perforated face 310 and through a diffusion barrier 312 (e.g., a precalibrated semi-permeable membrane). Detector 300 also includes a spacer 314, and a charcoal sorbent pad 316. The diffusion barrier creates a concentration gradient from its surface to the carbon sorbent pad.

In use, detectors are respectively positioned upstream or downstream of a filter to be monitor and left in place for a preselected period of time (t). After the preselected period, the detectors are sealed and typically taken to a lab for extraction of the adsorbed species. The pad is immersed in a solvent containing 1 μL of a 1.0 mg/mL cyclooctane/carbon disulfide solution. After a preselected period, the extract is decanted into a vial and reduced at ambient temperature and pressure in a low velocity fume hood. the final volume typically ranges from 0.5 mL to 5 1 μL. Sample volumes of 1–3 μL are injected into a gas chromatograph/mass spectrometer (e.g., a Hewlett-Packard 5992A GC/MS), which separates and identifies the adsorbed species. The identity of the molecular contamination and the collected masses of the respective components are used to calculate the concentration of the molecular contamination.

Molecular contamination 306 contacts the detection surface of monitor 300 by diffusion. At the surface of the screen the molecular contamination concentration is the air concentration (C) and at the sorbent pad the concentration is effectively zero. From Frick's First Law of Diffusion, it can be determined that $$C = \frac{m}{t \cdot u \cdot r} \quad (9)$$

where C is the molecular contamination concentration, m is the mass of substance adsorbed onto the sorbent pad, t is the sampling interval, u is the uptake rate, and r is the recovery coefficient (a factor used to adjust for incomplete extraction of a substance from the sorbent pad). The uptake rate (u) and the recovery rate (r) have been measured and published for a large number of organic vapors (e.g., 3M #3500 Organic Vapor Monitor Sampling Guide (Occupational Health and Safety Products Division/3M; December 1992) and 3M #3500 Organic Vapor Monitor Analysis Guide (Occupational Health and Safety Products Division/3M; 1981), both of which are herein incorporated by reference).

A filter monitor useful for monitoring formaldehyde has a similar construction as detector 300, except the adsorbent material is coated with a solution reactive with formaldehyde (e.g., an organic passive monitor available from Advanced Chemical Sensors Co. 4901 North Dixie Hwy. Boca Raton, Fla. 33431). Formaldehyde contamination in an air stream passes through a diffusion barrier and forms a non-volatile residue on the adsorbent material. The mass of formaldehyde formed on the adsorbent material may then be measured after a preselected exposure period in a manner similar to that described above in connection with the 3M filter monitor.

Passive Bubbler Monitor

Figure 5:
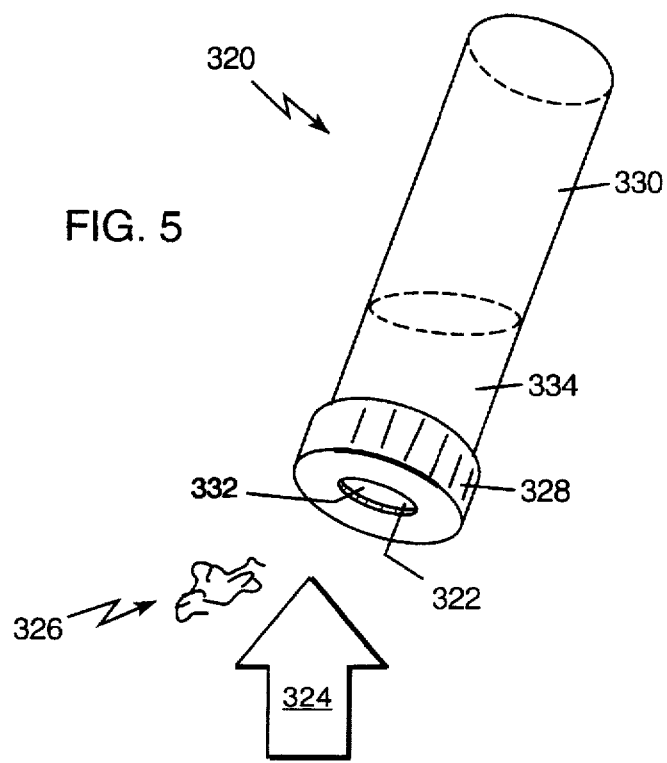
FIG. 5 is a diagrammatic perspective view of a detector.

Referring to FIG. 5, an alternative detector 320 (e.g., a PASSIVE BUBBLER™ available from SKC, Inc., 863 Valley View Rd., Eighty Four, Pa. 15330, and described in The PASSIVE BUBBLER™—A User's Manual, which is herein incorporated by reference), that may be used as upstream detector 20 or downstream detector 22, includes a detection surface 322 that is exposed to an incoming air stream 324 including molecular contamination 326 through a septum cap 328. Detector 320 includes a glass vial 330 sealed with a TEFLON®-faced Knudsen diffusion disk 332 retained by the septum cap. Vial 330 contains a water-based sorbent solution 334 that is particularly suited for adsorbing, e.g., ammonia, hydrogen chloride, hydrogen fluoride, sulfur dioxide and other water-soluble pollutants. In use, the vial is held with the disk side down so that the sorbent solution is in contact with the disk. A detector of this kind may also be adapted for monitoring formaldehyde (also available from SKC, Inc.).

The adsorption of contaminants is regulated by the Knudsen diffusion disk. Contaminants pass through the disk based on collisions with the walls defining the micropores of the disk. The disk enables liquid reagents to be used and provide accurate monitoring of certain molecular contaminants. The quantity of adsorbed contamination is determined by using calorimetry, GC, HPLC, ION specific electrode or other known techniques. In particular, once the adsorbed contaminants have been identified, the concentration (C) of each contaminant in the monitored air stream is determined by $$C = \frac{M}{D_{Kn} \cdot (A/L)} \qquad (10)$$

where $D_{Kn}$ is the observed Knudsen diffusion coefficient, A/L is the sampling area to pathlength ratio, and M is the rate of sample uptake give by $$M = \frac{70.2}{\sqrt{\text{mol. wt. of contaminant}}} \qquad (11)$$

Alternatively, the sampling rate may be obtained from the tabulated values, e.g., contained in The PASSIVE BUBBLER™—A User's Manual, or determined experimentally.

Matched Monitor

Figure 6:
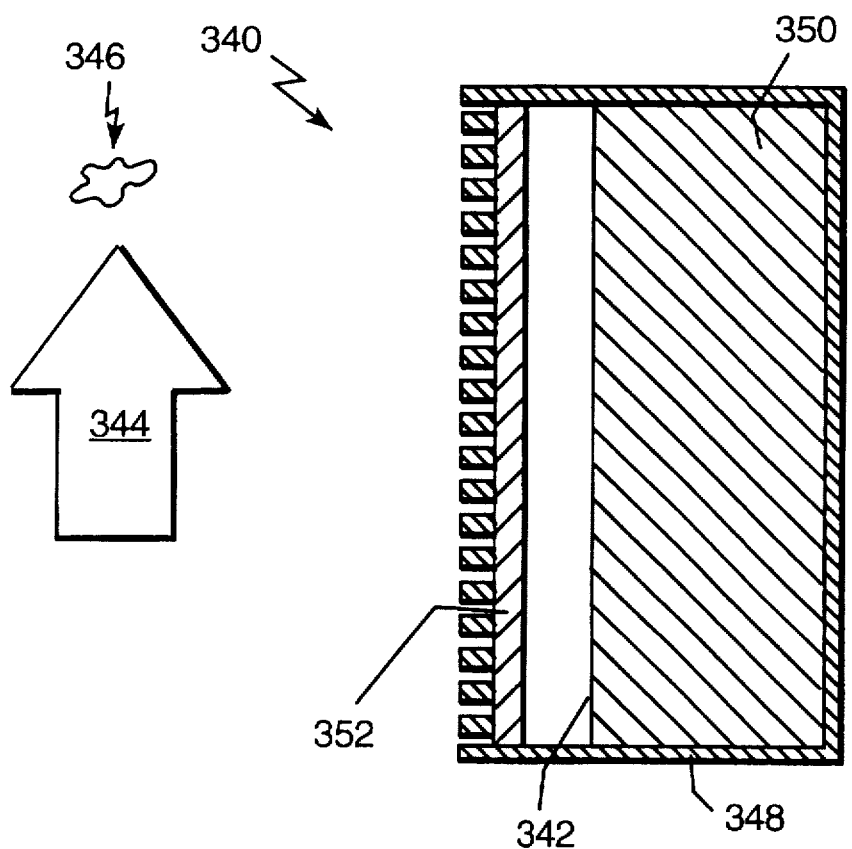
FIG. 6 is a diagrammatic cross-sectional side view of a detector.

Referring to FIG. 6, a detector 340, which may be used as upstream detector 20 or downstream detector 22, includes a detection surface 342, which is exposed to an incoming air stream 344 including molecular contamination 346. Detector 340 includes a housing 348 containing adsorbent media 350 (e.g., activated carbon particles with or without a reagent) and a diffusion barrier 352 that creates a diffusion gradient between the air stream and the adsorbent media. The adsorbent media is the same as that used in the gas-phase filter to be monitored. In this way detector 340 adsorbs the same gas-phase contamination as the filter with a similar sensitivity. This provide a highly accurate determination of the filter's performance. The adsorbed contamination is extracted in the same way as described above in connection with other adsorbent detectors.

Performance Analysis

Figure 7:
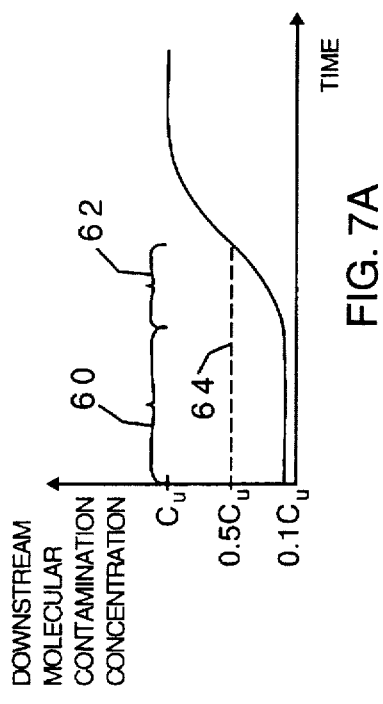
FIGS. 7 and 7A are plots of upstream and downstream molecular contamination concentrations over time, respectively.
Figure 7A:
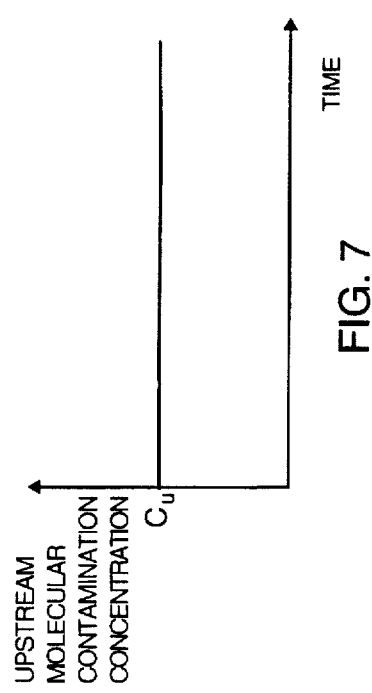

Referring to FIGS. 7 and 7A, assuming an airstream upstream of a gas-phase air filter is subject to a constant concentration ($C_{0,upstream}$; FIG. 7) of molecular contamination and assuming the gas-phase air filter has an efficiency profile over time similar to that shown in FIGS. 2–2B, we expect the concentration of molecular contamination in the airstream downstream of the gas-phase filter to vary over time as shown in FIG. 7A. In an initial part (60) of the service life of the filter, the efficiency ($\epsilon$) of the filter is generally constant at about 90% and the concentration of molecular contamination downstream of the filter is generally about 10% ($0.1 \cdot C_{upstream}(t)$) of the concentration upstream of the filter. During an intermediate stage (62) of the filter's service life, the efficiency of the filter drops off steadily as the adsorbent surfaces of the filter become used up by adhered molecular contamination. When the efficiency of the filter drops below a predetermined threshold level 64 (preferably below 30%–98%, and more preferably below 50%, depending on the sensitivity of the environment to molecular contamination), the filter should be replaced.

Figure 8:
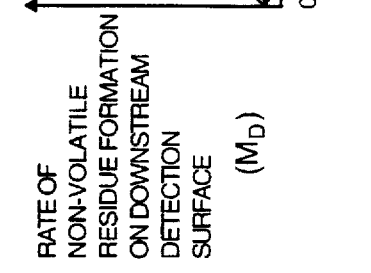
FIGS. 8 and 8A are plots of the rate of non-volatile residue formation on upstream and downstream detection surfaces over time, respectively.
Figure 8A:
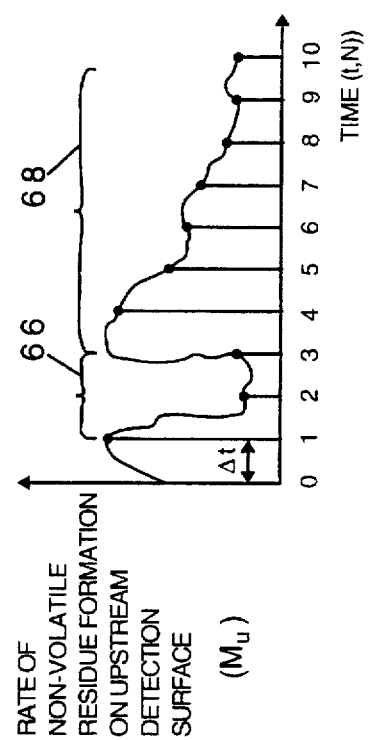

Referring to FIGS. 8 and 8A, the actual formation rate of non-volatile residue onto the detection surfaces of the upstream and downstream detectors not only depends on the varying molecular contamination concentrations in the respective airstreams, but also depends on other factors such as temperature, humidity, and the amount of material previously formed onto the detection surfaces; all of which change over time, creating artifacts in the measured signals. As shown in FIG. 8, the rate non-volatile residue forms onto the upstream detection surface exposed to upstream air having a constant concentration of molecular contamination may change significantly over time. For example, a significant drop 66 in the formation rate may result from a change in temperature or humidity. Also, a generally decreasing artifact 68 in the formation rate may be observed due to changes in the detection surfaces over time caused by previously formed material.

Similar trends may be observed in the rate of non-volatile residue formation on the downstream detection surface, as shown in FIG. 8A. However, a generally decreasing artifact, similar to artifact 68, should typically appear at a later time in the measured formation rate on the downstream detection surface because the rate of material formation on the downstream detection surface is less than the formation rate on the upstream detection surface. Also, superimposed onto these artifacts for the downstream detector are the changes in the concentration of molecular contamination in the airstream resulting from changes in filter efficiency; the desired quantity to be determined.

Referring to FIGS. 9 and 9A, the measured rates of non-volatile residue formation on the upstream and downstream detection surfaces may be used to obtain a measure representative of the efficiency of the gas-phase air filter. This allows the filter to be monitored to determine when the filter should be replaced. As shown in FIG. 9, the variations in the detectivities of the upstream and downstream detection surfaces do not substantially affect the effective efficiency of the filter calculated from equation (4) above. This is due to the fact that the downstream detection surface is exposed to similar environmental conditions that affect the upstream detection surface. Therefore, substantial variations in the measured concentration levels may be divided out to obtain a fairly good real-time measure of the filter efficiency.

The continuous changes in the rate of non-residue formation may be sampled at discrete times separated by $\Delta t$ (labeled 0–10 in FIGS. 8, 8A and 9A) instead of continuously. As shown in FIG. 9A, the sampled data can be used to determine the discrete effective efficiency ($\bar{\epsilon}_{eff}[N]$) over time, where $$\bar{\epsilon}_{eff}[N] = \frac{M_{upstream}[N] - M_{downstream}[N]}{M_{upstream}[N]} \qquad (9)$$

Referring to FIG. 10, the difference between the measured rates of upstream ($M_{upstream}$) and downstream ($M_{downstream}$) non-volatile residue formation substantially preserves the artifacts caused by, e.g., changes in environmental conditions. For example, drop 66 in the measured upstream molecular contamination concentration appears as a drop in the plot of $M_{upstream} - M_{downstream}$ because the filter acts proportionally on the upstream concentration levels and not on the basis of absolute quantity. Additionally, generally decreasing artifact 68 in the measured upstream concentration causes the general aspect of the $M_{upstream} - M_{downstream}$ plot to slope downwards (72) at a quicker rate that the drop in the actual filter efficiency because the upstream detection surface obtains more material formation than the downstream detection surface over a given period of time. This deviation from the actual filter efficiency is more pronounced in the $M_{upstream} - M_{downstream}$ plot than in the plot of effective efficiency (FIGS. 9 and 9A) because $M_{upstream}$ only appears in the denominator in the determination of $\epsilon_{eff}$ (which tends to flatten the curve).

Therefore, reliance upon a difference in the measured concentration levels (represented by measured rates of nonvolatile residue formation) would not provide an accurate measure of filter performance and may lead to frequent premature changes of the gas-phase filter, increasing operating costs. For example, a test for determining that a filter should be replaced could consist of comparing the difference between the measured upstream and downstream rates of non-volatile residue formation to a threshold value 74 and if the measured difference falls below the threshold value, the filter should be replaced. However, this test would have indicated that the filter would have to be replaced at time $t_r$, well before the time the filter should be replaced, simply because of an environmental change.

Figure 11:
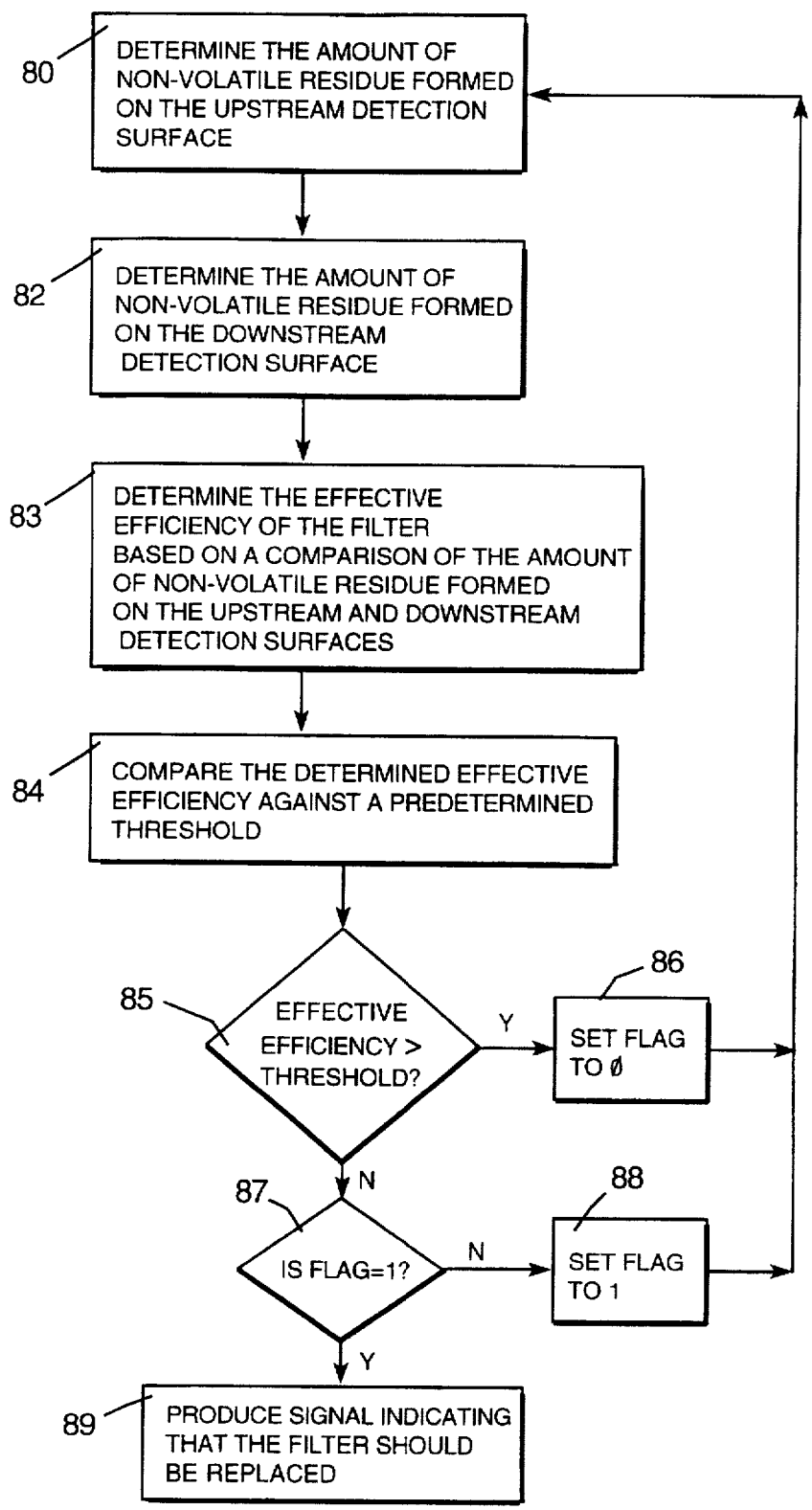
FIG. 11 is a flow diagram of a process for monitoring the performance of a gas-phase air filter

Referring to FIG. 11, in a presently preferred embodiment, the performance of a gas-phase filter is monitored as follows. The amount of non-volatile residue formed on the upstream detection surface is determined (80). The amount of non-volatile reside formed on the downstream detection surface is determined (82). The effective efficiency is determined based on a comparison of the amount of non-volatile residue formed on the upstream and downstream detection surfaces (83). The determined effective efficiency is compared against a predetermined threshold (84). If the effective efficiency is greater than the threshold (85), a flag variable is set to 0 (86) and the monitoring process is repeated. If the effective efficiency is less than the threshold and the flag variable is currently not equal to 1 (87), the flag is set to one and the monitoring process is repeated (88). If, on the other hand, the effective efficiency is less than the threshold the flag variable is equal to 1 (87), then a signal is produced indicating that the filter should be replaced (89).

In an alternative embodiment, the flag variable may be compared against an integer greater than 1 at step (87) and the flag variable may be increased incrementally at step (88) to enhance the accuracy of verification procedure (steps 85–88) before the filter replacement signal is produced (89).

APPLICATIONS

Cleanroom Recirculating Air System

Figure 12:
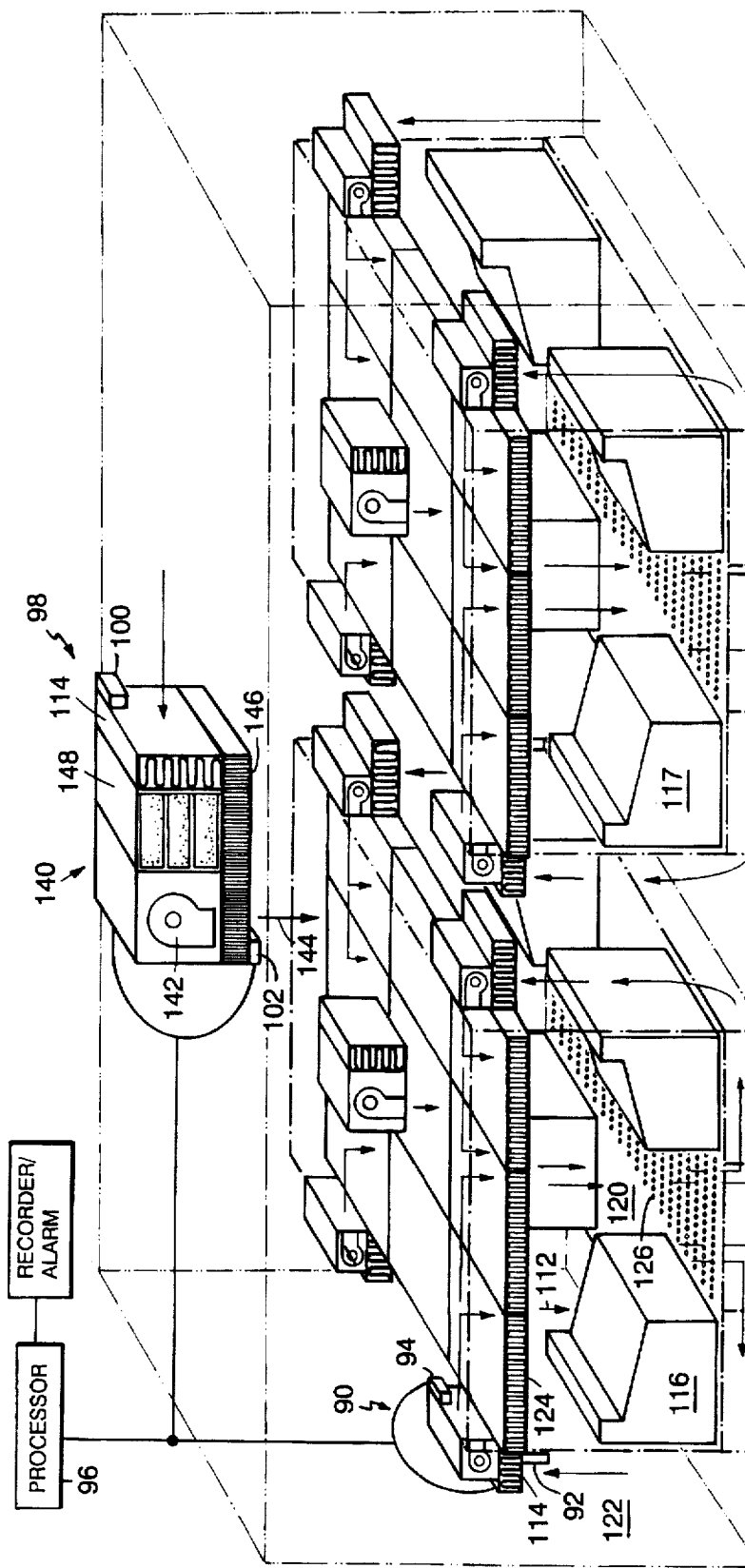

Referring to FIGS. 12 and 12A, inside a cleanroom 110 molecular contaminants (too small to be shown) in recirculating air streams 112 are removed by chemically active molecular air filter 114 (e.g., a VAPORSORB® chemical filter available from Extraction Systems, Inc. of Woonsocket, R.I., USA), at least some of which having sequentially arranged upstream and downstream air filtering beds selected for effective targeted removal of process-limiting molecular contamination from the air streams in a manner reducing self-contamination and cross-contamination of process stations 116, as described in U.S. Ser. No. 08/317,315, filed Oct. 4, 1994, which is herein incorporated by reference. An example of a process station includes a conventional semiconductor photolithography station 117, although other processing stations are contemplated including etch, chemical vapor formation, thin film deposition, developing, epitaxy and diffusion stations. Such process-limiting molecular contaminants may be released into the air streams by process stations 116.

Each processing station 116 is associated with a recirculating air handling system that generates recirculating air streams 112 (e.g., with air blowers 118). air stream recirculation rate is on the order of ten interchanges (on the order of 2000 cu.ft./cycle) per minute to thoroughly filter the air streams even when the molecular filters are near the end of their respective service lives. A higher recirculation rate can compensate for the inevitable decrease in efficiency. For example, after ten air cycles a filter with a 30% efficiency may reduce the level of air contamination by 99%. An air stream 112 follows a path which includes, a process station 116, a floor 120, a common air plenum 122, an air filter 114, a filter monitor 90 including upstream and downstream detectors 92, 94 and a high efficiency particulate air (HEPA) filter 124 used to remove particulate contamination (e.g., dust, lint, and other debris) from the air stream. The floor 120 is a conventional cleanroom floor that has air passages 126 to allow air streams 112 to pass therethrough.

Each filter monitor 90 includes a respective upstream detector 92 and a respective downstream detector 94 which may be coupled to a processor 96 for comparing real-time signals from detectors 92, 94 to determine an effective efficiency of filter 114, depending on the type of monitor employed. If the effective efficiency of a filter falls below a predetermined threshold level (e.g., below 50%–99%, and more preferably below 80%–98%), processor 96 produces a signal indicating that the filter should be replaced. Upstream and downstream detectors 92, 94 are preferably configured as a mass microbalance resonator sensor, as described above, that can detect a broad class of condensable molecular contamination at concentration levels down to 1 ppb.

TARGETED REMOVAL

Example 1

For the effective targeted removal of ammonia and other reactive amines from the vicinity of a deep UV photolithography station, detectors 92, 94 having a construction similar to detector 320 (FIG. 5) containing a solution including an acid reagent, e.g., hydrochloric acid, citric acid, oxalic acid, phosphorous acid, and sulfuric acid, are positioned upstream and downstream of a gas-phase air filter, as described in U.S. Ser. No. 08/317,315, filed Oct. 4, 1994. Alternatively, detectors 92, 94 may be similar to detector 30 (FIG. 3) coated with one of the acid reagents recited above. The acid reacts with amine contamination ($R(NH_x)$) to produce a solid by-product at the detection surfaces:

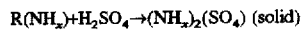

$R(NH_x) + H_2SO_4 \rightarrow (NH_x)_2(SO_4)$ (solid)

The quantity of acid used to treat the detection surfaces is minimal and non-volatile so that the treatment does not contribute to the molecular contamination in the vicinity of the deep UV station.

Example 2

For the effective targeted removal of molecular contamination including acid gases or acid vapors from the vicinity of an etch station, detectors 92, 94 having a construction similar to detector 320 (FIG. 5) containing a solution including a basic reagent, e.g., KI, $K_2CO_3$, NaOH, $Na_2CO_3$, or an organic base such as an organic amine, are positioned upstream and downstream of a gas-phase air filter, as described in U.S. Ser. No. 08/161,931, filed Dec. 2, 1993, which is herein incorporated by reference. Alternatively, detectors 92, 94 may be similar to detector 30 (FIG. 3) coated with one of the basic reagents recited above. The base reacts with acid contamination ($H_xR$) to produce a solid by-product at the detection surfaces:

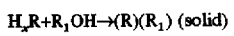

$H_xR + R_1OH \rightarrow (R)(R_1)$ (solid)

The quantity of base used to treat the detection surfaces is minimal and non-volatile so that the treatment does not contribute to the molecular contamination in the vicinity of the deep UV station.

Example 3

For the effective targeted removal of molecular contamination including corrosive gases or vapors (e.g., $H_2S$, HCl, HF, $Cl_2$, $SO_2$, and $H_2SO_4$) from a cleanroom, detectors 92, 94 coated with a thin film of a corrodible material that corrodes when exposed to such corrosive gases or vapors, e.g., aluminum, silver, copper or a chemical coating such as TRIS (2-amino-2-hydroximethyl-1,3-propanediol), are positioned upstream and downstream of a gas-phase air filter, as described in U.S. Ser. No. 08/161,931, filed Dec. 2, 1993. The corrosive gases and vapors react with the applied metal layer to produce a solid by-product at the detection surfaces:

corrodible layer+corrosive gas→solid at surface

A corrosion monitor of this type includes a quartz crystal microbalance plated with either copper or silver is the ONGUARD™1000 electronic corrosion sensor available from $A^3$, and described in the ONGUARD™ Installation and Operation Manual, which is herein incorporated by reference.

Example 4

For the effective targeted removal of molecular contamination including organic gases or organic vapors from the vicinity of a pre-gate oxidation area of a cleanroom detectors 92, 94 with uncoated (e.g., bare piezoelectric crystal material is exposed to the contamination) detection surfaces are positioned upstream and downstream of a gas-phase air filter, as described in U.S. Ser. No. 08/161,931, filed Dec. 2, 1993. The organic contamination deposits on the clean crystal surface, which is detected as a resonant frequency shift.

Alternatively, detectors 92, 94 having a construction similar to detector 300 (FIG. 4) or detector 340 (FIG. 6) may be used. The adsorbent media used for this application comprises activated carbon.

Make-up Air System

A make-up air handling system 140 is used to replace the air removed from the vicinity of the processing stations by the exhaust systems with air from, e.g., a sub-fab area. Air blower 142 generates the make-up air stream 144. A HEPA filter 146 is located downstream of the blower to prevent fine particulate contaminants from entering the common air plenum 122. An efficient (about 70%) particulate bag filter 148 is located upstream of the HEPA filter to prevent loading of the HEPA filter. A chemically active air filtering system 114, which generally has a particulate removal efficiency of about 30%, is located at an inlet port of the make-up air handling system to prevent premature loading of the bag and HEPA filters and filter molecular contamination from the incoming make-up air streams.

A filter monitor 98, including upstream and downstream detection surfaces 100, 102, is used to monitor the efficiency of the chemical filters in the make-up air system. Filter monitor 98 is configured in a similar manner as monitor 90 and is also coupled to processor 96 to provide real-time evaluation of the make-up air filters. The detection surfaces of the detectors are coated with a layer of, e.g., aluminum, silver, copper or a plastic layer such as TRIS (2-amino-2-hydroximethyl-1,3-propanediol) to selectively detect corrosive gases or vapors. Alternatively, the detection surfaces are uncoated to detect organic molecular contamination such as hydrocarbons.

In an alternative embodiment, detectors 100, 102 having a construction similar to detector 300 (FIG. 4) or detector 340 (FIG. 6) is used. The adsorbent media used for this application comprises activated carbon to detect organic molecular contamination such as hydrocarbons. Additional monitors having a construction similar to detector 320 (FIG. 5) are used upstream and downstream to detect corrosive gases or vapors.

Residential or Commercial Building

Figure 13:
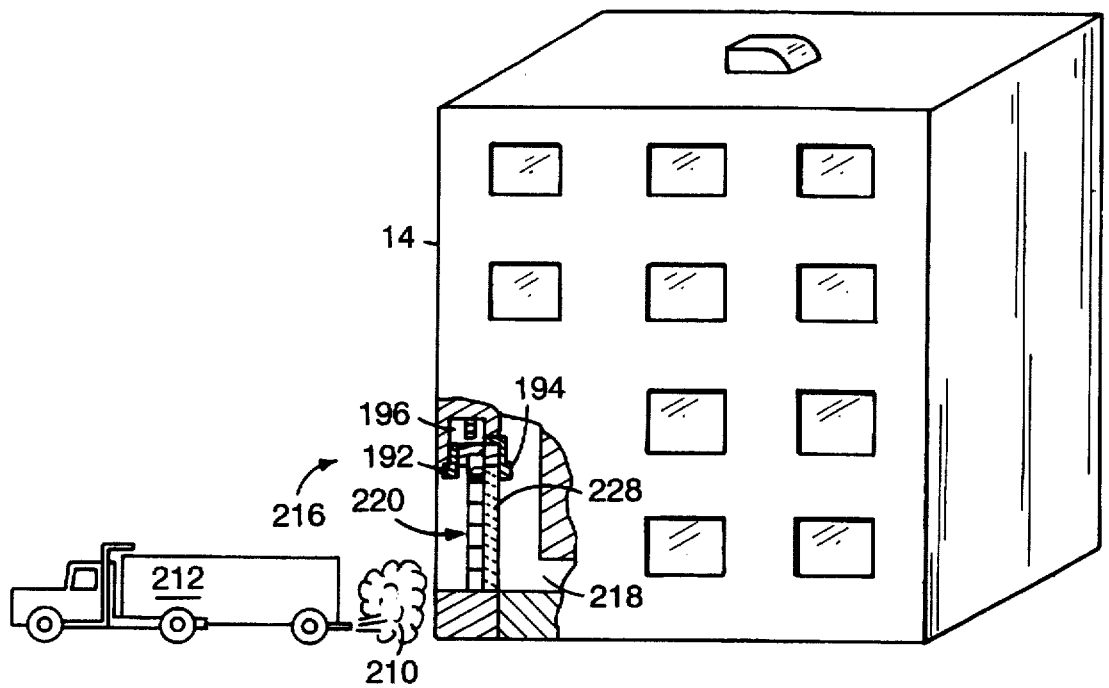
FIG. 13 is a perspective view, partially broken away, of a building with an air handling system and a truck idling proximal to the building.
Figure 13A:
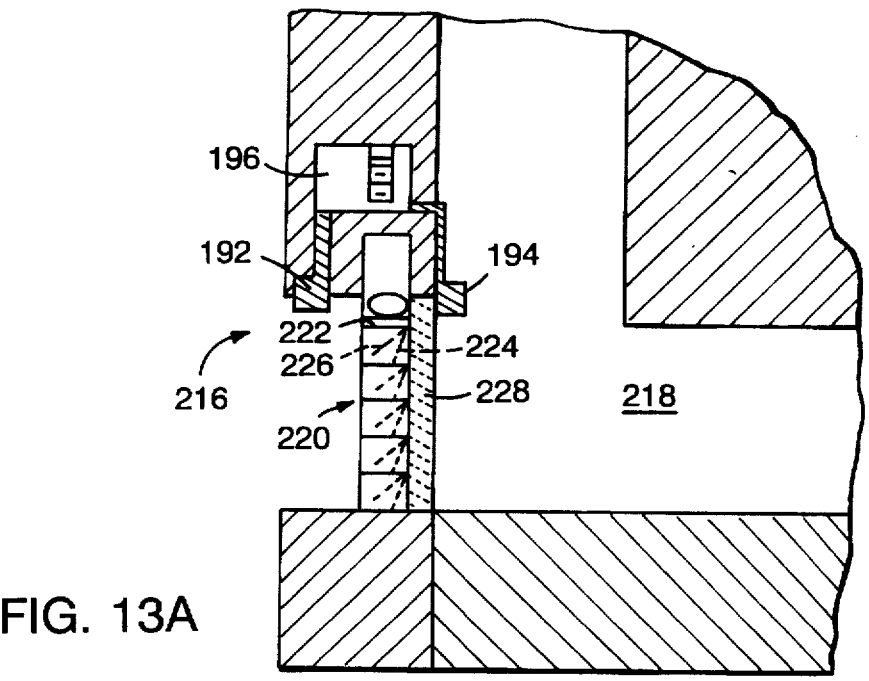
FIG. 13A is an expanded view of the building air handling system shown in FIG. 13.

Referring to FIGS. 13 and 13A, pollutants 210 (e.g., diesel fuel combustion by-products) are discharged from the exhaust system of a delivery truck 212 that is idling while items are being transferred from the truck to a building 14. The truck is parked proximal to an air intake port 216 of the building's air system. The air system comprises air blowers that draw outside air into the building, and a network of air ducts 218 for circulating the air throughout the building. As shown in FIG. 12A, located at the intake port 216 is a damper 220 that can be maintained in an open position 222, a closed position 224, or an intermediate position 226. When the damper is in the closed position 224, it substantially blocks the flow of air through the intake port 216, thereby preventing pollutants 210 from being drawn into building 214. A sorbent-based filter 228 (e.g., a Vaporsorb® chemical filter available from Extraction Systems, Inc. of Woonsocket, R.I., U.S.A.) is employed to substantially remove pollutants 210 from the air flowing past damper 220.

A filter monitor 190 includes a detector 192 positioned upstream of filter 228 and a detector 194 positioned downstream of filter 228. Detectors 192, 194 are coupled to a processor 196 for comparing real-time signals from detectors 192, 194 to determine an effective efficiency of filter 228. If the effective efficiency of a filter falls below a predetermined threshold level (e.g., below 30%–60%, and more preferably below 50%), processor 196 produces a signal indicating that the filter should be replaced.

Upstream and downstream detectors 192, 194 are preferably configured as a mass microbalance sensor, as described above, that can detect a broad class of condensable molecular contamination at concentration levels down to 1 ppb, or less. The detection surfaces of the detectors are coated with a layer of, e.g., aluminum, silver, copper or a plastic layer such as TRIS (2-amino-2-hydroximethyl-1,3-propanediol) to selectively detect corrosive gases or vapors. Alternatively, the detection surfaces may be uncoated to detect organic molecular contamination such as hydrocarbons.

In an alternative embodiment, detectors 192, 194 having a construction similar to detector 300 (FIG. 4) or detector 340 (FIG. 6). The adsorbent media used for this application comprises activated carbon to detect organic vapor molecular contamination. Additional monitors having a construction similar to detector 320 (FIG. 5) are used upstream and downstream to detect corrosive gases or vapors.

Other embodiments are within the scope of the claims.

For example, more than one pair of upstream and downstream detectors may be employed to monitor filter performance. In this case, the respective detection surfaces of the detectors may be selectively coated to detect different broad classes of molecular contamination (e.g., organic contamination, acid contamination, and base contamination). The different broad classes may overlap.

A filter monitor 145 may be associated with an activated carbon chemically active molecular air filtering system 150 (FIG. 12A) installed inside a processing station 146 which has an independent air handling system.

It is also contemplated that filter monitors can be associated with filters within a self-contained processing station (a so-called "mini-environment") that includes its own respective air handling system, instead of sharing a common clean environment (e.g., a cleanroom) with other processing stations.

Still other embodiments are within the scope of the claims.

What is claimed is:

1. A method for monitoring the performance of a gas-phase filter positioned in an air stream, which may be subject to molecular contamination, and useful for removing molecular contamination therefrom, the method comprising the steps of:
    exposing an upstream detection surface to the airstream at a location upstream of the air filter so that a variety of upstream molecular contaminants may form non-volatile residue on the exposed upstream detection surface over time;
    exposing a downstream detection surface to the airstream at a location downstream of the air filter so that a variety of downstream molecular contaminants may form a non-volatile residue on the exposed downstream detection surface over time;
    determining the mass of non-volatile residue respectively formed on the exposed upstream and downstream detection surfaces; and
    determining the performance of the air filter based on the ratio of the determined mass of non-volatile residue respectively formed on the exposed upstream and downstream detection surfaces.

2. The method of claim 1 wherein the step of determining the performance of the air filter comprises determining an effective efficiency ($\epsilon_{\it eff}$) of the filter as defined by $$\epsilon_{\it eff} = \frac{M_{upstream} - M_{downstream}}{M_{upstream}}$$

wherein $M_{upstream}$ and $M_{downstream}$ are the amount of non-volatile residue formed on the upstream and downstream detection surfaces respectively.

3. The method of claim 1 wherein said step of determining the performance of the air filter comprises determining the rates of change in the amounts of non-volatile residues forming on said upstream and downstream detection surfaces over preselected sequential intervals of time.

4. The method of claim 3 wherein said step of determining the rates of change further comprises determining an effective efficiency ($\epsilon_{\it eff}$) of the filter as defined by $$\epsilon_{\it eff} = \frac{\Delta m_{upstream} - \Delta m_{downstream}}{\Delta m_{upstream}}$$

wherein $\Delta m_{upstream}$ and $\Delta m_{downstream}$ are the changes in the amounts of non-volatile residues formed on said upstream and downstream detection surfaces during a preselected interval of time.

5. The method of claim 1 wherein the step of determining the amount of non-volatile residue comprises determining the mass of non-volatile residue respectively formed on the exposed upstream and downstream detection surfaces.

6. The method of claim 1 wherein the step of determining the amount of non-volatile residue comprises generating electrical signals representative of the amount of non-volatile formed on said detection surfaces.

7. The method of claim 1 wherein said steps of exposing upstream and downstream detection surfaces to the airstream comprise the step of providing a mass microbalance sensor.

8. The method of claim 7 wherein said step of providing a mass microbalance sensor comprises providing a surface acoustic wave mass microbalance.

9. The method of claim 8 wherein said step of providing a mass microbalance sensor comprises providing a piezoelectric crystal mass microbalance.

10. The method of claim 1 wherein the upstream detection surface and the downstream detection surface that are respectively exposed to the airstream comprise adsorbent media separated from the air stream by a diffusion barrier.

11. The method of claim 1 wherein the gas-phase filter being monitored comprises adsorbent media and the upstream detection surface and the downstream detection surface each comprises substantially the same kind of adsorbent media as the gas-phase filter.

12. The method of claim 1 wherein said upstream and downstream detection surfaces that are exposed to the air stream are sensitive to levels of molecular contamination in the concentration range of 1 ppm to 1 ppb, or less.

13. The method of claim 1 wherein said upstream and downstream detection surfaces that are exposed to the airstream are sensitive to organic condensables.

14. The method of claim 1 wherein said upstream and downstream detection surfaces that are exposed to the airstream are selected so that a preselected type of molecular contamination preferentially forms a non-volatile residue on the exposed upstream and downstream detection surfaces.

15. The method of claim 14 wherein said upstream and downstream detection surfaces that are exposed to the airstream are each treated with a reagent comprising a base so that acid vapors preferentially form non-volatile residues thereon.

16. The method of claim 14 wherein said upstream and downstream detection surfaces that are exposed to the airstream are each treated with a reagent comprising an acid so that basic vapors preferentially form non-volatile residues thereon.

17. A method for monitoring the performance of a gas-phase filter positioned in an air stream, which may be subject to molecular contamination, and useful for removing molecular contamination therefrom, said method comprising the steps of:
    exposing an upstream detection surface to the airstream at a location upstream of the air filter so that a variety of upstream molecular contaminants may form non-volatile residue on the exposed upstream detection surface over time;
    providing a first electrical signal representative of the mass of non-volatile residue formed on the upstream detection surface;
    exposing a downstream detection surface to the airstream at a location downstream of the air filter so that a variety of downstream molecular contaminants may form a non-volatile residue on the exposed downstream detection surface over time;
    providing a second electrical signal representative of the mass of non-volatile residue formed on the downstream detection surface; and
    determining in real-time the performance of the air filter based on the first and second electrical signals that are provided.

18. A filter monitor for determining the performance of a gas-phase filter positioned in an air stream, which may be subject to molecular contamination, and useful for removing molecular contamination therefrom, said filter monitor comprising:
    an upstream piezoelectric detector having a detection surface exposed to the airstream at a location upstream of the air filter so that molecular contamination may form a nonvolatile residue on the exposed detection surface of the upstream detector, said upstream detector having an output for providing a signal representative of the increase in mass of non-volatile residue formed on the detection surface of the upstream detector;

a downstream piezoelectric detector having a detection surface exposed to the airstream at a location downstream of the air filter so that molecular contamination may form a non-volatile residue on the exposed detection surface of the downstream detector, said downstream detector having an output for providing a signal representative of the increase in mass of non-volatile residue formed on the downstream detector; and a comparator having an input coupled to said upstream and downstream detectors and having an output for providing an output signal representative of the performance of the air filter based on the ratio of signals received from said upstream and downstream detectors.

19. The filter monitor of claim 18 wherein said comparator provides an output representative of an effective efficiency ($\epsilon_{\mathit{eff}}$) of the filter as defined by $$\epsilon_{\mathit{eff}} = \frac{M_{upstream} - M_{downstream}}{M_{upstream}}$$

wherein $M_{upstream}$ and $M_{downstream}$ are the amounts of non-volatile residue formed on the upstream and downstream detection surfaces respectively.

20. The filter monitor of claim 18 wherein said comparator provides an output representative of the efficiency of the filter based on the rates of change in the mass of non-volatile residues formed on the exposed detection surface of said upstream and downstream detectors over preselected intervals of time.

21. The filter monitor of claim 20 wherein said comparator provides an output representative of an effective efficiency ($\epsilon_{\mathit{eff}}$) of the filter as defined by $$\epsilon_{\mathit{eff}} = \frac{\Delta M_{upstream} - \Delta M_{downstream}}{\Delta M_{upstream}}$$

wherein $\Delta M_{upstream}$ and $\Delta M_{downstream}$ are the changes in the mass of non-volatile residues formed on the exposed detection surfaces said upstream and downstream detectors during a preselected interval of time.

22. The filter monitor of claim 18 wherein said upstream and downstream detectors each comprise a mass microbalance sensor.

23. The filter monitor of claim 22 wherein each of said mass microbalance sensors comprises a surface acoustic wave mass microbalance.

24. The filter monitor of claim 23 wherein each of said mass microbalance sensors comprises a piezoelectric crystal mass microbalance.

25. The filter monitor of claim 18 wherein said upstream and downstream detectors are sensitive to levels of molecular contamination in the concentration range of 1 ppb to 1 ppm.

26. The filter monitor of claim 18 wherein said upstream and downstream detectors are sensitive to organic condensables.

27. The filter monitor of claim 19 wherein said upstream and downstream detectors are selected so that preselected types of molecular contamination preferentially form on the exposed detection surfaces of said detectors.

28. The filter monitor of claim 27 wherein the exposed detection surfaces of said upstream and downstream detectors are each treated with a reagent comprising a base so that acid vapors preferentially form non-volatile residues thereon.

29. The filter monitor of claim 27 wherein the exposed detection surfaces of said upstream and downstream detectors are each treated with a reagent comprising an acid so that basic vapors preferentially form non-volatile residues thereon.

30. A filter monitor for determining the performance of a gas-phase filter positioned in an air stream, which may be subject to molecular contamination, and useful for removing molecular contamination therefrom, said filter monitor comprising:

an upstream piezoelectric detector having a detection surface exposed to the airstream at a location upstream of the air filter so that molecular contamination may form a non-volatile residue on the exposed detection surface of the upstream detector, the detection surface of said upstream detector being selected so that the increase in mass of non-volatile residue formed on the detection surface of the upstream detector may be determined;

a downstream piezoelectric detector having a detection surface exposed to the airstream at a location downstream of the air filter so that molecular contamination may form a non-volatile residue on the exposed detection surface of the downstream detector, the detection surface of said downstream detector being selected so that the increase in mass of non-volatile residue formed on the detection surface of said downstream detector may be determined; and means for determining the performance of the air filter based on the mass of non-volatile residue formed on the upstream detection surface and based on the mass of non-volatile residue formed on the downstream detection surface.

31. The filter monitor of claim 30 wherein said upstream detector and said downstream detectors are mass microbalance sensors.

32. The filter monitor of claim 30 wherein said upstream detector and said downstream detector each comprises adsorbent media selected to remove the molecular contamination and separated from the airstream by a diffusion barrier.

33. The filter monitor of claim 30 wherein the gas-phase filter comprises adsorbent media and the upstream detection surface and the downstream detection surface each comprises substantially the same kind of adsorbent media as the gas-phase filter.

\* \* \* \* \*